(12) United States Patent
Neuenschwander

(10) Patent No.: US 9,937,083 B1
(45) Date of Patent: Apr. 10, 2018

(54) ANTI-CHANNELING STOOL MANAGEMENT SYSTEM

(71) Applicant: Lois Jean Neuenschwander, Oneco, FL (US)

(72) Inventor: Lois Jean Neuenschwander, Oneco, FL (US)

( * ) Notice: Subject to any disclaimer, the term of this patent is extended or adjusted under 35 U.S.C. 154(b) by 692 days.

(21) Appl. No.: 14/475,571

(22) Filed: Sep. 2, 2014

Related U.S. Application Data

(63) Continuation-in-part of application No. 13/422,783, filed on Mar. 16, 2012, now Pat. No. 8,821,460, which is a continuation-in-part of application No. 12/655,853, filed on Jan. 8, 2010, now Pat. No. 8,382,734.

(51) Int. Cl.
*A61F 13/49* (2006.01)
*A61F 13/495* (2006.01)
*A61F 13/475* (2006.01)
*A61F 13/15* (2006.01)

(52) U.S. Cl.
CPC .......... *A61F 13/475* (2013.01); *A61F 13/495* (2013.01); *A61F 2013/1513* (2013.01); *A61F 2013/49087* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 2,529,999 | A | * | 11/1950 | Chambers | A61F 13/496 604/347 |
| 3,103,930 | A | * | 9/1963 | Collett | A41B 13/06 604/355 |
| 3,522,807 | A | * | 8/1970 | Millenbach | A61F 5/451 604/344 |
| 3,734,096 | A | * | 5/1973 | Millenbach | A61F 5/441 604/355 |
| 4,784,656 | A | * | 11/1988 | Christian | A61F 5/4408 604/332 |
| 4,834,737 | A | * | 5/1989 | Khan | A61F 13/4915 604/385.14 |
| 4,850,986 | A | * | 7/1989 | Temple | A61F 5/44 604/332 |
| 5,312,384 | A | * | 5/1994 | Temple | A61F 5/44 604/355 |

(Continued)

*Primary Examiner* — Todd J Scherbel
*Assistant Examiner* — Guy K Townsend

(57) ABSTRACT

A stool management and collection system for acutely and chronically ill patients that prevents stool channeling and the consequential breakdown of patient skin. It comprises a bandage unit, a contour pad, a backing member, an easily connectible and releasable fastener, and a stool holding bag with a tapered upper portion. In addition, a diaper is used to collect patient urine and support the stool holding bag in approximately the same area where an incontinence pad is worn, instead of on the patient's backside as in the prior art. Furthermore, the opening in the bandage unit should leave a minimum distance of approximately three-sixteenths of an inch around the patient's rectal opening for the application of barrier cream or other skin-protecting substance. Super absorbent polymer (SAP) resin may be employed as a part of the system's structure, and a liner may be added to the stool collection bag.

8 Claims, 11 Drawing Sheets

(56) References Cited

U.S. PATENT DOCUMENTS

| | | | | |
|---|---|---|---|---|
| 5,421,827 A * | 6/1995 | Temple | A61F 5/451 | 383/67 |
| 5,741,239 A * | 4/1998 | Mulholland | A61F 5/451 | 604/328 |
| 5,941,860 A * | 8/1999 | Wheeler | A61F 5/451 | 604/327 |
| 6,355,022 B1 * | 3/2002 | Osborn, III | A61F 13/47209 | 604/330 |
| 6,432,096 B1 * | 8/2002 | McFall | A61F 13/47209 | 604/385.17 |
| 6,582,411 B1 * | 6/2003 | Carstens | A61F 13/15723 | 604/385.01 |
| 6,635,799 B1 * | 10/2003 | Osborn, III | A61F 13/47209 | 604/367 |
| 7,537,587 B2 * | 5/2009 | Carstens | A61F 13/47254 | 604/385.01 |
| 7,727,218 B2 * | 6/2010 | Lavon | A61F 13/15203 | 604/385.09 |
| 7,763,003 B1 * | 7/2010 | Yip | A61F 13/505 | 604/385.01 |
| 7,766,887 B2 * | 8/2010 | Burns, Jr. | A61F 13/15585 | 604/385.14 |
| 7,771,406 B2 * | 8/2010 | Mueller | A61F 13/15609 | 604/385.01 |
| 7,772,455 B1 * | 8/2010 | Roe | A61F 13/42 | 604/360 |
| 7,867,211 B2 * | 1/2011 | Carstens | A61F 13/47254 | 604/385.01 |
| 8,062,277 B2 * | 11/2011 | Fleming | A61F 13/47209 | 604/359 |
| 8,382,734 B1 * | 2/2013 | Neuenschwander | A61F 13/495 | 604/385.09 |
| 8,821,460 B1 * | 9/2014 | Neuenschwander | A61M 3/0279 | 604/319 |
| 8,939,952 B2 * | 1/2015 | Weig | A61F 2/0027 | 604/101.05 |
| 2003/0120178 A1 * | 6/2003 | Heki | A61F 5/455 | 600/574 |
| 2006/0264883 A1 * | 11/2006 | Carstens | A61F 13/4704 | 604/396 |
| 2006/0264885 A1 * | 11/2006 | Carstens | A61F 13/47254 | 604/396 |
| 2007/0142816 A1 * | 6/2007 | Carstens | A61F 13/47254 | 604/396 |
| 2007/0255239 A1 * | 11/2007 | Hataya | A61F 5/451 | 604/319 |
| 2010/0022976 A1 * | 1/2010 | Weig | A61F 2/0027 | 604/355 |
| 2010/0274209 A1 * | 10/2010 | Roe | A61F 13/42 | 604/378 |
| 2013/0190706 A1 * | 7/2013 | Kleiner | A61F 13/00068 | 604/319 |

* cited by examiner

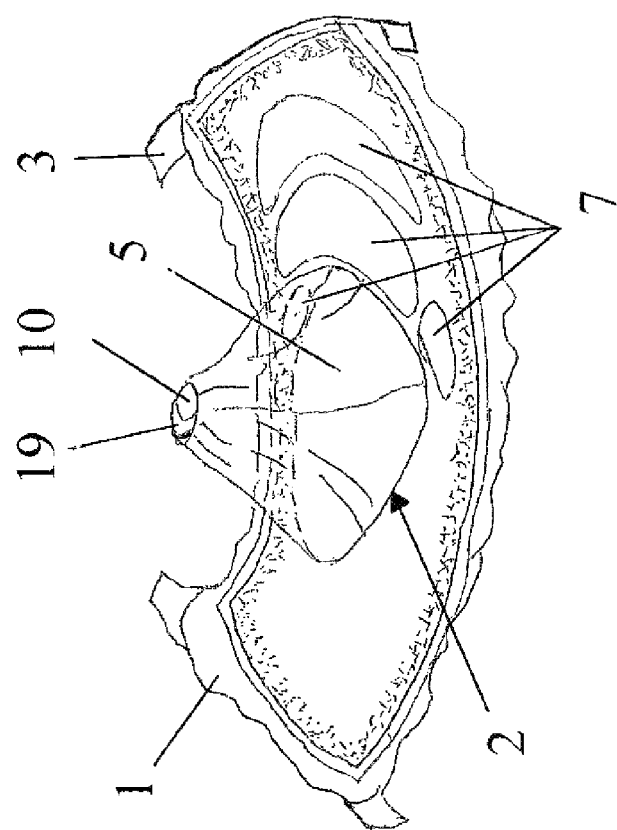
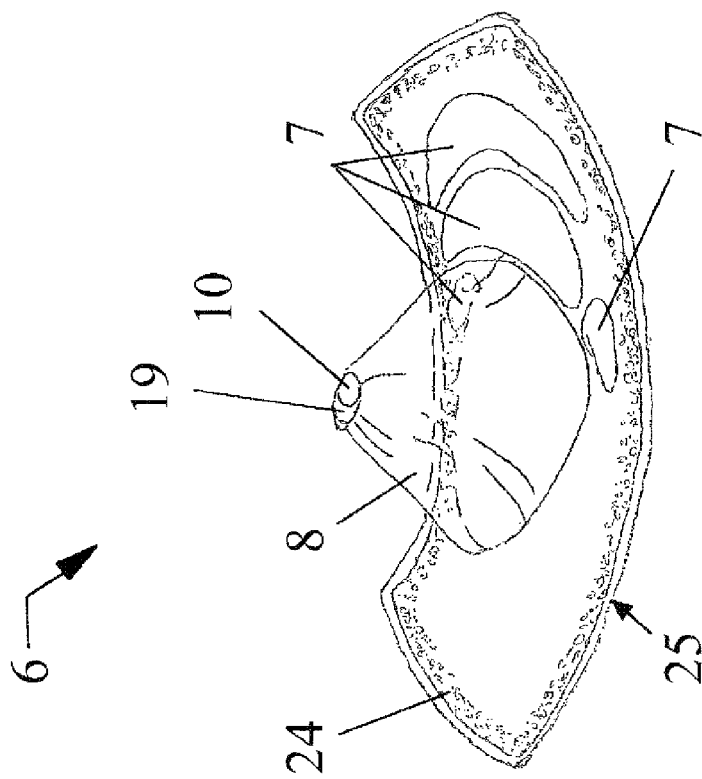
FIG. 3b
FIG. 3a

ANTI-CHANNELING STOOL MANAGEMENT SYSTEM

CROSS REFERENCES TO RELATED APPLICATIONS

This invention relates in part to aspects of two U.S. patent applications previously filed by the same applicant herein, the first of which was entitled "Adult Diaper System" and filed on Jan. 8, 2010 with a patent application number of Ser. No. 12/655,853, now U.S. Pat. No. 8,382,734 having an Issue Date of Feb. 26, 2013, and the second of which was entitled "Anti-Channeling Stool Management System" and filed on Mar. 16, 2012, with a patent application number of Ser. No. 13/422,783, scheduled to be issued as U.S. Pat. No. 8,821,460 on Sep. 2, 2014. The invention of the instant patent application of the applicant and both of her prior art patent applications disclose inventions that improve stool management and secure a stool collection container close to the patient's skin via a bandage. In addition, the inventions disclosed in all three patent applications can at least optionally employ hook-and-loop fasteners and all incorporate a free-zone around the bandage's opening in an attempt to prevent stool channeling. Furthermore, all inventions tackle the issue of incorrect positioning of the stool containing device on the buttocks that is common to prior art devices. Additionally, all of these inventions offer an option to avoid the indignity of a standard diaper that catches stool next to a patient's skin, which can quickly lead to skin breakdown. Thus, as a result of the common structure disclosed in the applicant's two above-identified patent applications, which are also found in the instant invention, the inventor herein respectfully requests that domestic priority be granted for the current patent application herein based upon the inventor's previously-filed patent applications identified hereinabove.

BACKGROUND

Field of the Invention

The present invention is in the field of devices used for stool incontinence management, and since it has structure that is free of the flaws commonly found in prior art stool incontinence management devices, the present invention both facilitates stool management and prevents the spread of disease that would otherwise be prevalent with discharge of infectious stool (such as C-diff, etc.) into a diaper. Use of the present invention system would save lives, and would also significantly reduce the large material and labor cost now associated with the care of stool incontinent patients worldwide, as it shifts the focus of stool incontinence management from diapers to stool collectors and it employs diapers only for urine collection and stool collector support. This allows frequent repeat use of the diapers after removal of a used stool holding bag and its placement by a new one using a quick release and attachment fastener secured between the backing member associated with the stool holding bag and a bandage unit that remains attached to the patient. The contour pads used between the bandage unit and the backing member attached to the top edge of the present invention stool holding bag may also be reused if unsoiled, as is considered appropriate by the patient's caregiver.

Stool collectors are the solution to reducing the spread of infectious disease. However, they cannot be used when a patient has skin breakdown, which occurs rapidly during prior art stool collector use, perhaps as early as 1-2 days after first use. The flaws and disadvantages which have been consistently associated with prior art devices in the field of stool incontinence management, and which are now overcome during use of the present invention stool incontinence management system, are: 1) skin breakdown under the bandage component of a stool collector (known as channeling), and channeling requires a discontinuation of use of the device until patient skin is healed; 2) devices becoming torn off while non-comatose patients move about in their beds, which often occurs and results in skin tears that can also require discontinuation of the stool collector until patient skin is healed; 3) lodging of semi-formed stool in the prior art devices, making them unusable and requires a discontinued use of the stool collector even when infectious semi-formed stool is present; and 4) a decrease in patient dignity and comfort when stool is deposited into a diaper.

Description of Related Art

The present invention is configured to stop the spread of stool borne infectious disease, but may also be used with patients having non-infectious incontinent stools to reduce the labor cost associated with the care of patients with incontinent stools and enhance patient comfort. Prior art stool collectors are known, however, they are not widely used, as the leakage of liquid stool under the collector's bandage and subsequent skin breakdown of patient skin in the areas of liquid stool contact, called channeling, have made prior art stool collectors useless in stopping the spread of stool borne disease.

*Clostrium difficile* (also referred to herein as *C. difficile* or C-diff) is a commonly-known bacterium that is currently being spread at alarming rates during patient care in U.S. hospitals and long-term care facilities, largely as a result of the overuse of certain antibiotics. Worldwide problems with C-diff infections also occur. *C. difficile* can cause diarrhea, as well as life-threatening inflammation or perforation of the colon. It is also is a spore-releasing bacterium, and is resistant to some antibiotics. Alcohol-based hand sanitizers do not kill the dormant *C. difficile* spores, nor does hand washing with soap and water. In addition, special bleach cleansers are required to stop the spread of infection once *C. difficile* spores come into contact with other surfaces where they can survive for weeks or months. Also, once spores come into contact with hospital uniforms, bed linens, and diapers, the spores can travel widely throughout a hospital or long-term care facility, as only a long soaking in bleach will kill them. The number of C-diff infections has increased significantly during the last 20-30 years due to the incomplete containment of diarrhea run-off, and recently became a leading healthcare-associated infection, surpassing the number of infections due to methicillin-resistant *Staphylococcus aureus* (MRSA).

Although fecal transplantation therapy (transplant of stool from a healthy human donor) is helping some C-diff patients recover and patient deaths from C-diff are peaking in 2014, during the last several years an estimated three million patients annually in the United States are infected with C-diff, resulting in over 110,000 patients deaths. Dealing with the cleanup of diarrhea in hospital and long-term care facilities is always time-consuming and expensive, with cost estimates for hospital-acquired *C. difficile* often exceeding $4,000 per patient. Traditional treatments for diarrhea have included diapers, creams, ointments, skin breakdown fixes such as sterile bandages and medications, and sufficient labor to keep the patient clean so that skin healing can occur. Prior art stool collection devices may stay in place for a maximum time period of 1-2 days, being removed more frequently should stool leakage occur, as repeat or extended contact with liquid stool quickly causes breakdown of patient skin. Also, when channeling of diarrhea under a bandage that holds a stool collector in place occurs and causes the breakdown of patient skin, use of the stool collection device must be discontinued, resulting in the increased opportunity for spread of C-diff and other infectious diseases to others. Annual diaper cost for one hundred patients with diarrhea is estimated at more than $200,000, and the annual cost of creams for one hundred diarrhea patients may add another $20,000 to the cost of patient care. Staff labor costs for those same one hundred patients may approach $1 million, with disposal cost for used diapers estimated at approximately $32,000. Thus, the approximate cost of treating one hundred diarrhea patients is close to $1.25 million per year. Furthermore, it is estimated that on any given day in U.S. hospitals more than 7,000 patients have a C-diff infection, leading to more than 3 million people infected in U.S. hospitals with C. difficile annually. Thus, the treatment costs of hospital-acquired or nursing home-onset of diarrhea in the U.S. as a result of C-diff infection is now estimated to be approximately a $12-to-14 billion annual expense. It is also estimated that one-third of patients with a C. difficile diagnosis return to a hospital with a recurrence of the disease. Since the present invention prevents channeling its use would break the chain of infection and slow down or stop the current C. difficile epidemic, and would also significantly reduce the high cost currently experienced by hospitals and long-term care facilities for the treatment of C-diff infections. In addition, if a patient gets a hospital-acquired C-diff infection, the hospital then becomes responsible for the cost of hospital care for the remainder of the patient's stay. In addition, if the patient has a recurrence of C-diff, on the patient's return, the hospital is also responsible for the cost/expenses for the return visit.

Another difficulty in the use of prior art stool collectors (which is overcome by present invention use), is that its positioning is on the backside of a patient in bed, and when a patient slides down, the bandage adhering the stool collector to the patient's skin pulls off, often tearing the skin. Another deficiency in prior art stool collectors, is that as a patient with serious diarrhea heals, the diarrhea gradually turns into a formed stool which can get stuck in the opening of a stool collector, making prior art stool collectors dysfunctional and necessitating their removal from the patient for the remainder of the patient's recovery. The present invention offers solutions that overcome all of these deficiencies. No invention is known that has the same features as the present invention, its same structure, or provides the same benefits and advantages to a user as the present invention.

BRIEF SUMMARY OF THE INVENTION

The primary objective of this invention is to provide a stool incontinence management device or system that overcomes the flaws of prior art stool collection devices and methods. Another objective of this invention is to provide a stool incontinence management medical device or system that diminishes the spread of C-diff and other infectious diseases present in human stool. It is also an objective of this invention to provide a stool incontinence management medical device or system that lessens the breakdown of patient skin. A further objective of this invention is to bring advances into low-tech, hands-on patient care that has had much fewer changes over the years than high-tech medical instruments and devices. It is a further objective of this invention to provide a stool incontinence management medical device or system that lowers the labor involved in hands-on care of patients, particularly those with skin breakdown as a result of channeling. A further objective of this invention is to change medical practice by lowering the cost of labor and materials used per patient. It is also an objective of this invention to provide a medical device or system that prevents the loss of patient dignity.

The present invention is a stool management and collection system mainly for acutely and chronically ill patients that prevents channeling which can quickly lead to the breakdown of patient skin, patient discomfort, and the spread of infectious disease. Since patients are so varied in size, it is contemplated for the present invention to be produced in multiple sizes, such as small, medium, and large, although not limited thereto, to make certain channeling does not occur. Although more than one preferred embodiment is disclosed herein, each has a bandage unit incorporating hook-and-loop attachment means, a stool holding bag with a tapered upper portion, and a contoured pad, the combination of which can be used with any brand of diaper, or as an integral part of a system having a diaper component with an interior configured to collect and hold urine away from patient skin, while stool is directed into an associated stool holding bag. The diaper also assists in supporting the weight of the stool holding bag as it fills. The diameter of the opening in the bandage unit should leave a minimum distance of approximately three-sixteenths of an inch around the patient's rectal opening for the application of barrier cream or other sealing substance. Super absorbent polymer (SAP) resin is a preferred part of the contoured pad, or other substance that can absorb approximately 40% to 60% of its weight in as long it had no toxic, irritating, or corrosive properties that might adversely affect patient skin. Furthermore, the present system's stool collection bag isn't positioned on the patient's backside as in the prior art, instead being secured in approximately the same area where an incontinence pad is typically positioned, so that diarrhea is contained from start to finish, even in the final stages when it is semi-solid. Four preferred embodiments of the present invention are disclosed herein, however, the scope of the present invention should not be considered as limited thereto, and one should consult the appended claims for a determination of the full structure and scope of the present invention.

BRIEF DESCRIPTION OF THE SEVERAL VIEWS OF THE DRAWINGS

FIG. 3a is a perspective view from the top of a diaper insert (stool holding bag with a liner) providing the second preferred embodiment of the present invention that is similar to the stool holding bag shown in FIG. 2a, and showing the non-tapered bottom portion of the stool holding bag with urine transfer holes/areas, and also showing the tapered top portion of the stool holding bag extending in an upwardly direction, and a backing member and opening associated with the top end of the tapered portion of the stool holding bag which are used to assist the transfer of stool from a patient to the stool holding bag without leakage or channeling of patient skin.

FIG. 3b is a perspective view from the top of the non-tapered bottom portion of the diaper insert shown in FIG. 3a inside the diaper shown in FIGS. 1a, 1b, and 2b.

COMPONENT LIST

Figures 1A, 1B:
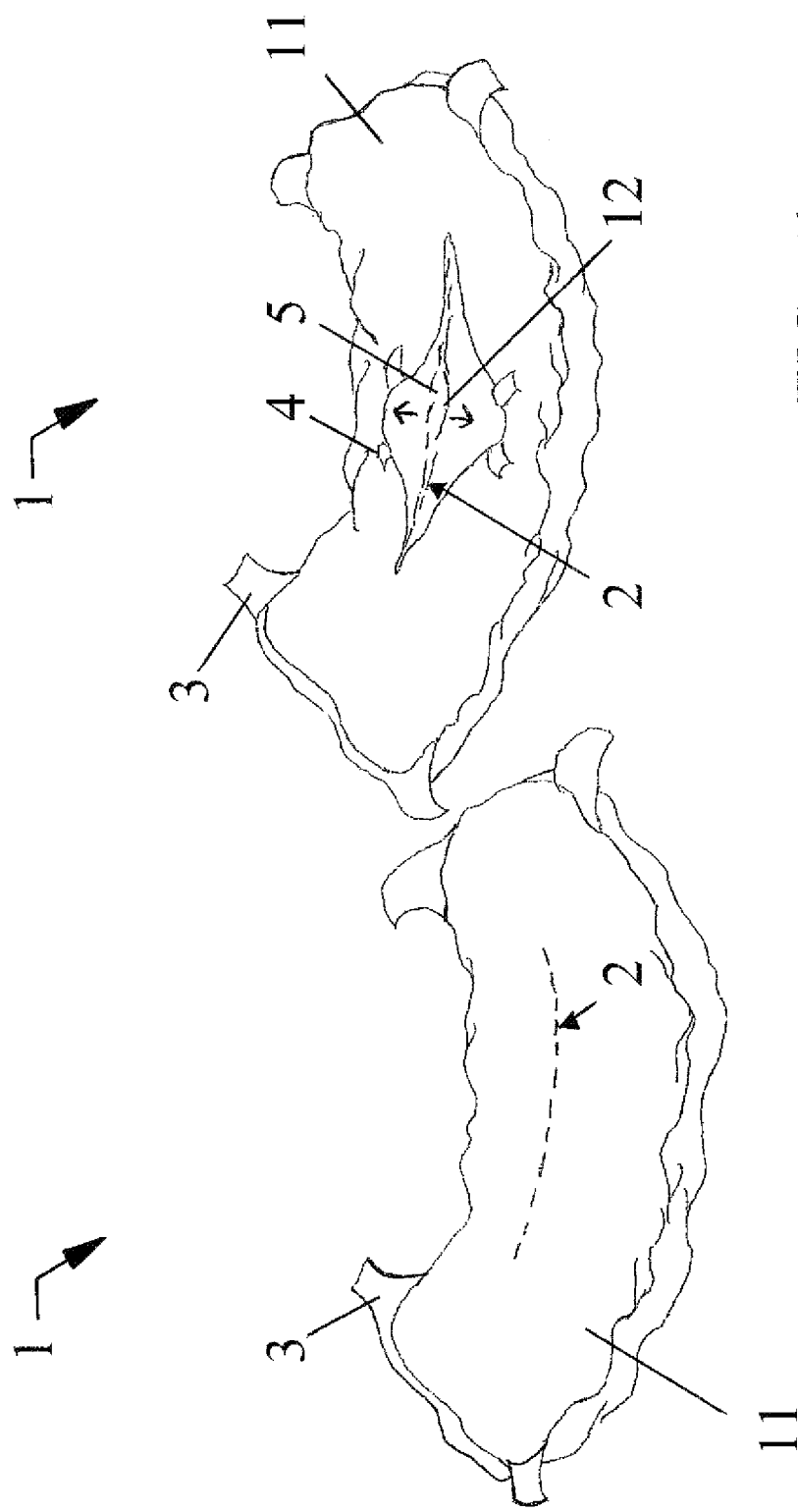
FIG. 1a is a perspective view from the top of a diaper usable with a first preferred embodiment of the anti-channeling stool management systems of the present invention to support its stool holding bag in a desired position of use as it fills, and showing an optional cut line for insertion of the stool holding bag of the present invention that allows repeat use of the diaper at least once in many stool incontinence management applications.
FIG. 1b is a perspective view from the top of the diaper in FIG. 1, and showing the cut line open and attachable adhesive strips used to create and maintain an opening during insertion of the non-tapered bottom portion of the stool holding bag of the present invention.

1 Diaper
2. Cut line
3. Adhesive fasteners
4. Pull tabs
5. Opening in diaper 1
6. Stool holding bag
7. Urine transfer holes/areas in non-tapered bottom portion of Stool holding bag 6
8. Tapered upper portion of stool holding bag 6
9. Bandage unit with Adhesive surface 26 and hook portion 22 of a 2-part fastener
10. Transfer opening in stool holding bag 6 for stool entry
11. Top filament of diaper 1
12. Absorbent interior of diaper 1 (fiberfill or other absorbent material, also preferably contains a core of SAP)
13. Contoured pad (shaped to fit against a patient's body)
14. Biasing area of bandage unit 9
15. Assembly (Backing member 19 in a position to bias Contoured pad 13 toward patient 16 and loop portion of 2-part fastener attached to Backing member 19)
16. Patient
17. Anti-reflux valve
18. Cutting tool
19. Backing member
20. Top edge of tapered upper portion 8 around transfer opening 10
21. Loop portion of 2-part fastener
22. Hook portion of 2-part fastener 23. Skin protecting composition
24. Stool absorbing liner positioned within Stool holding bag 6
25. Non-tapered bottom portion of Stool holding bag 6
26. Attachment area between Top edge 20 of Stool holding bag 6 and Backing member 19
27. Adhesive surface of Bandage Unit 9
28. Rectal opening of Patient 16
29. Cutting head of Cutting tool 18
30. Handle of Cutting tool 18

DETAILED DESCRIPTION OF THE INVENTION

Figure 4:
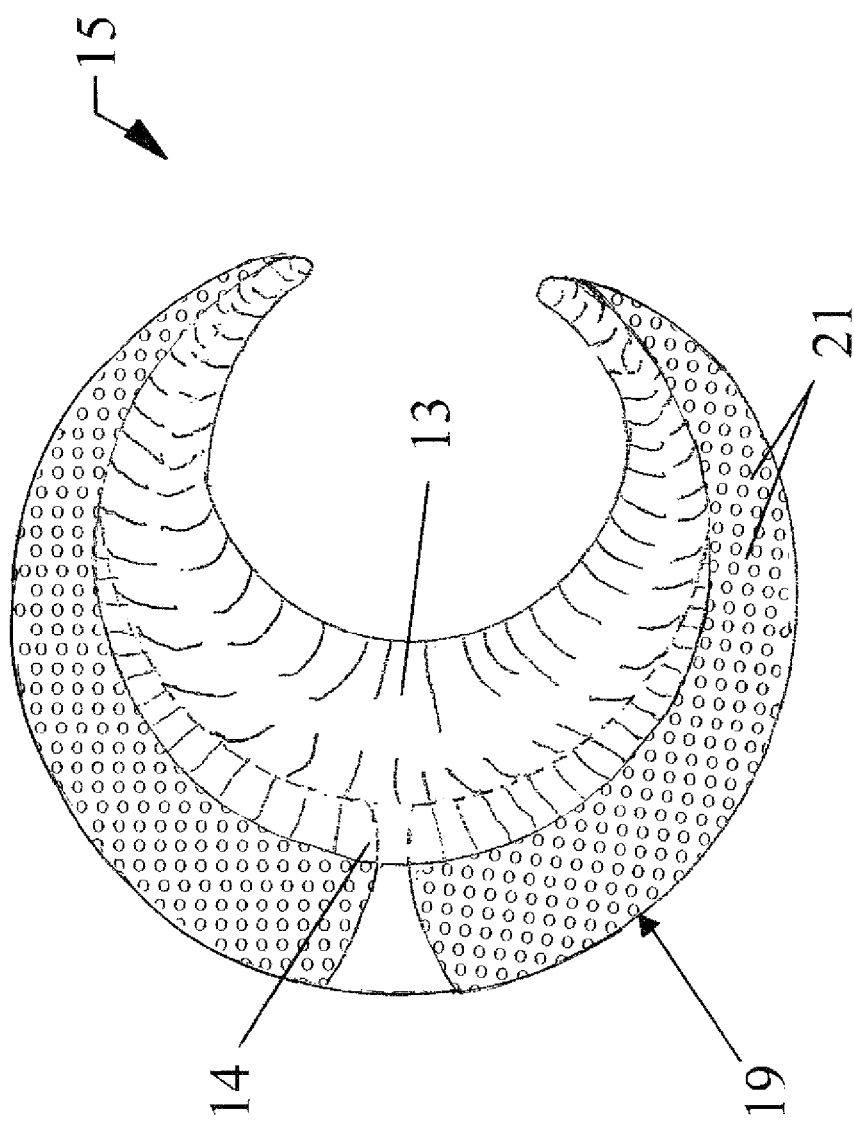
FIG. 4 is a top view of the generally C-shaped backing member used as a part of preferred embodiments of the present invention, which is shown having the loop portion of a 2-part fastener attached to it that can be releasably secured to the hook portion of the 2-part fastener secured to the bandage unit shown in FIGS. 6a and 6b, with the exterior perimeter curved edge of a present invention absorbent contour pad shown partially overlapping the backing member so that the surface of the contoured pad can be secured by the backing member which biases it against the bandage unit in a position where the contoured pad can absorb any small amount of stool that is adjacent to the opening in the stool holding bag and not readily transferred into it.
Figure 5:
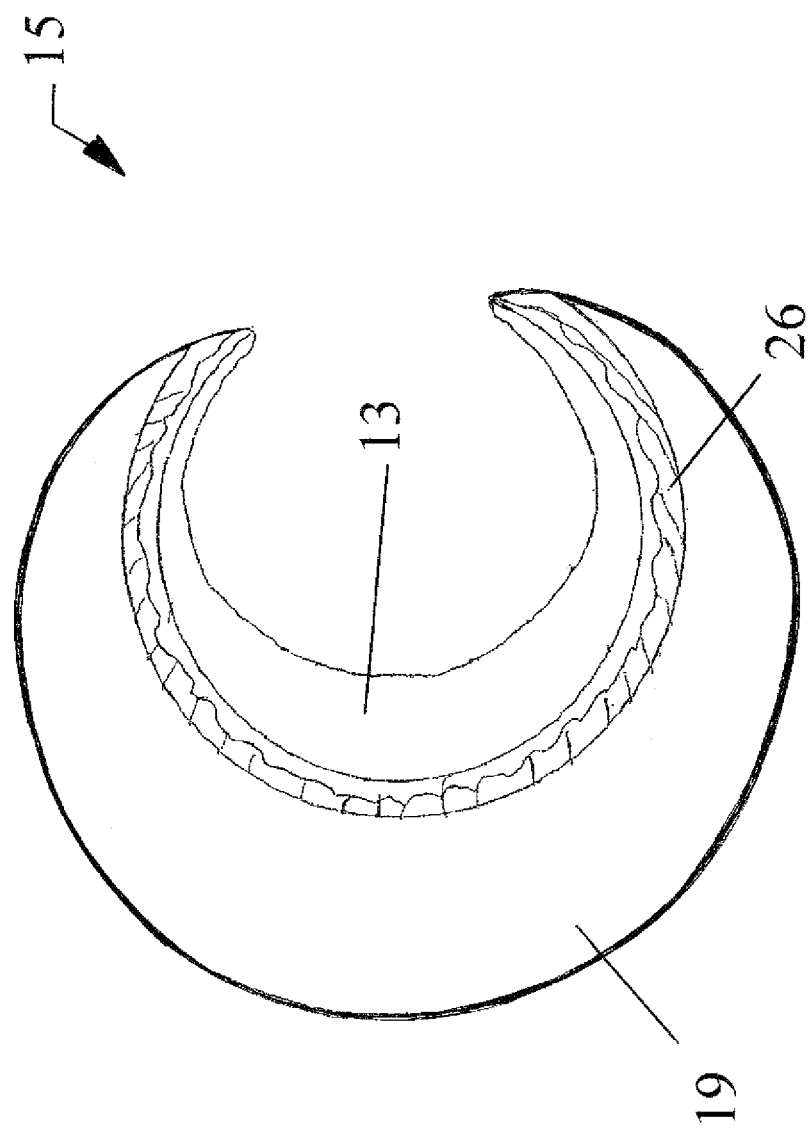
FIG. 5 is a bottom view of the generally C-shaped backing member shown in FIGS. 2a, 2b, 3a, and 3b, with FIG. 5 showing it attached to the top edge of the present invention stool holding bag and the backing member overlapping part of an absorbent contoured pad used as a part of the present invention adjacent to patient skin near the rectal opening, with the loop portion of a hook-and-loop fastener secured out-of-view on the reverse side of the backing member.
Figure 6A:
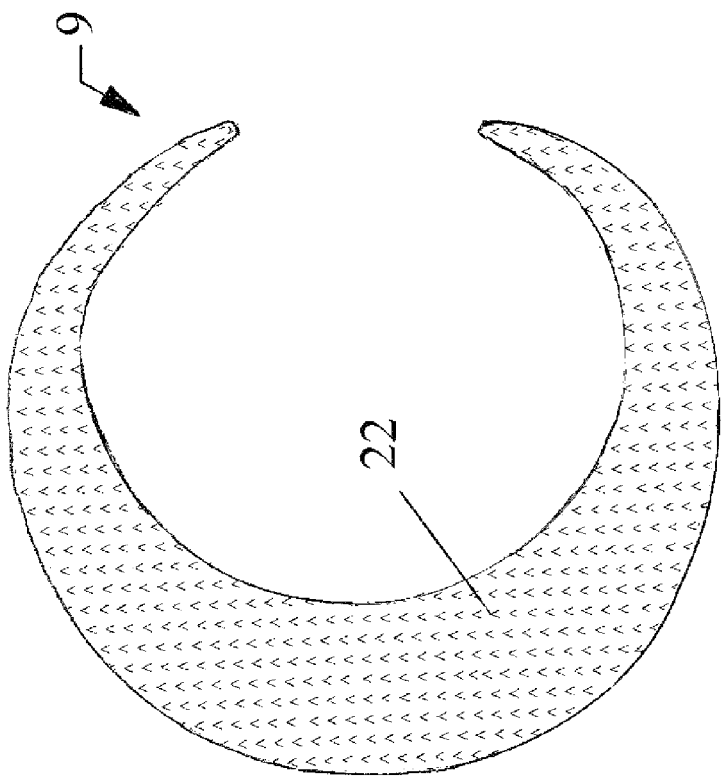
FIG. 6a is a bottom view of the generally C-shaped bandage unit having the hook portion of a hook-and-loop fastener secured to it, and showing the hook fasteners substantially covering the exterior surface of the bandage unit that during use is positioned away from the patient's skin and available to connection to the loop portion of a hook-and-loop fastener secured to the backing member attached to the top edge of the present invention stool holding bag.
Figure 6B:
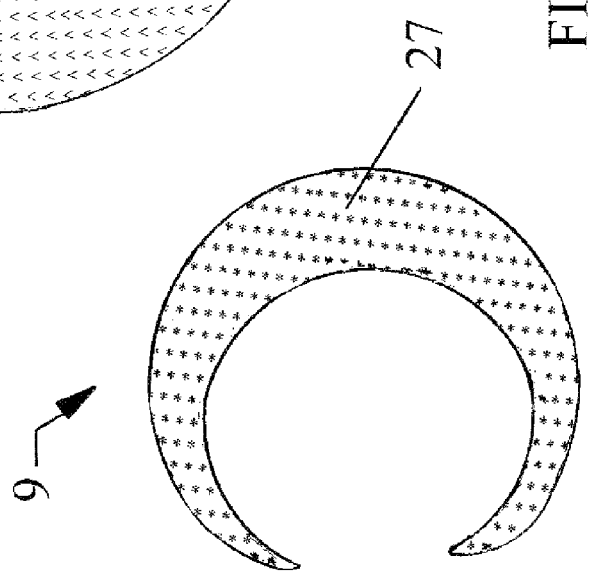
FIG. 6b is a top view of the generally C-shaped bandage unit having adhesive secured to it for attachment of the bandage unit to patient skin, that allowing its reverse side shown in FIG. 6a to become secured to the backing member attached to the top edge of the present invention stool holding bag.
Figure 7:
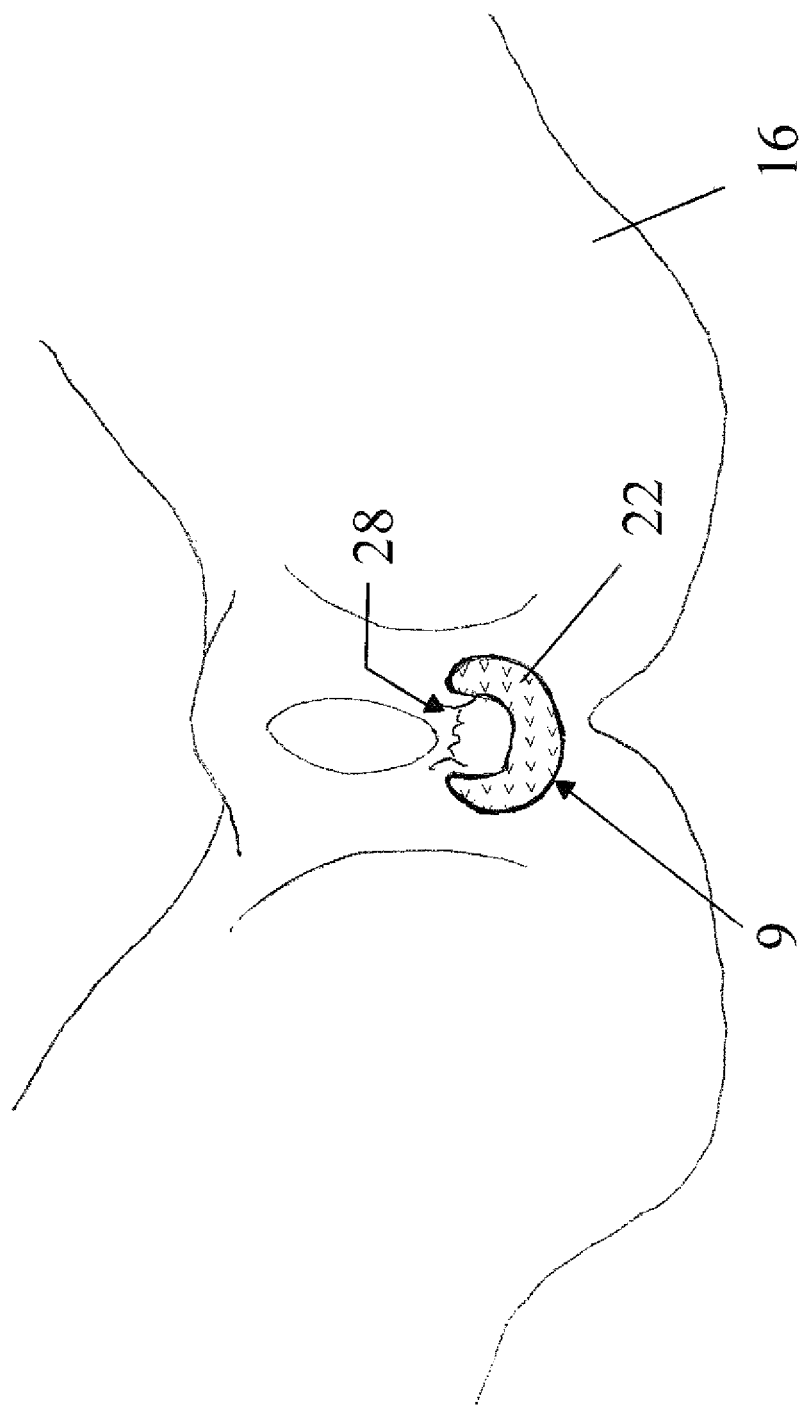
FIG. 7 is an enlarged view of the anal area of a patient with the generally C-shaped bandage unit used as a part of the most preferred embodiments of the present invention in its position of use rearward from the rectal opening, with the hook portion of a hook-and-loop fastener visible and the adhesive out-of-view on the reverse side of the bandage unit positioned out-of-view.
Figure 8:
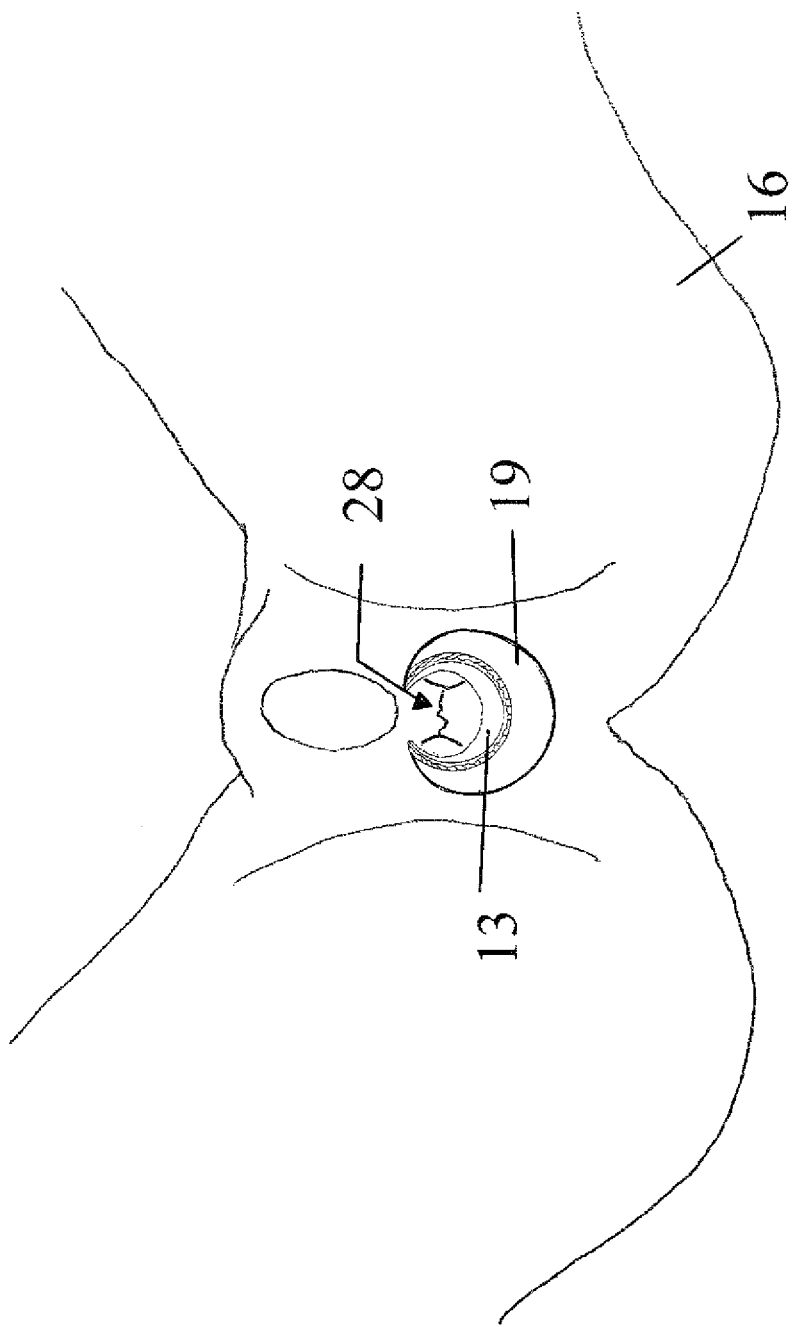
FIG. 8 is an enlarged view of the anal area of a patient with the combined backing member and contoured pad shown in FIG. 5 and used as a part of the most preferred embodiments of the present invention in their positions of use rearward from the rectal opening.
Figure 9:
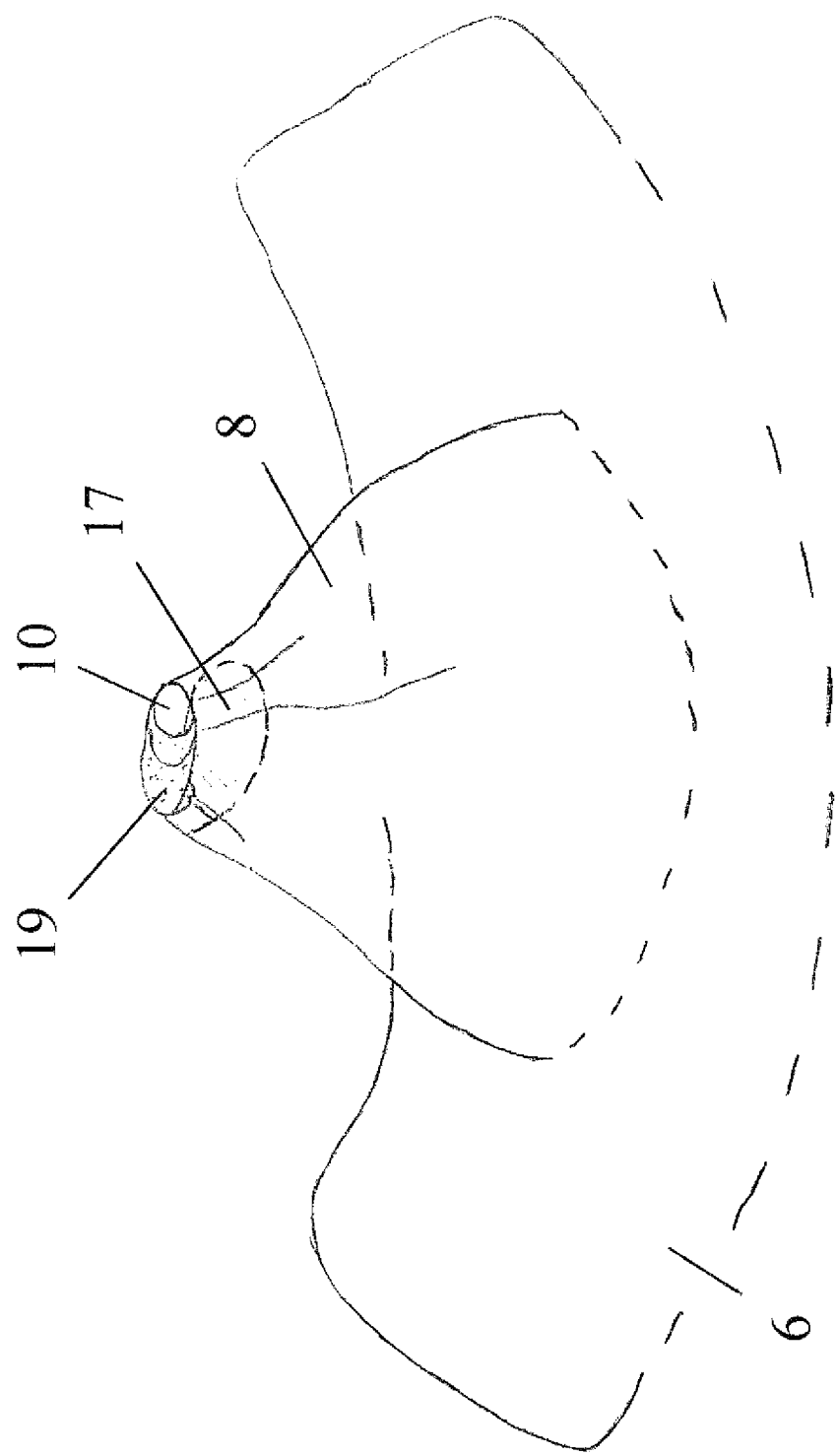
FIG. 9 is a perspective view from the top of the stool holding bag in a third preferred embodiment of the present invention with a flap of plastic positioned to block the top opening in the stool holding bag in a manner that prevents reflux movement of stool from the stool holding bag and upward toward the patient.

The present invention is a stool management and collection system for acutely and chronically ill patients 27 that prevents channeling which can quickly lead to the breakdown of patient 16 skin, patient 16 discomfort, and the spread of disease. Although four preferred embodiments are disclosed herein, all have a contoured pad 13, a bandage unit 9 with a hook portion 22 of a 2-part fastener, a stool holding bag 6 with a tapered upper portion 8, and a backing member 19 secured to the top edge 20 of the tapered upper portion 8 of the stool holding bag 6 and having the loop portion 21 of a 2-part fastener secured to the one of its opposed surfaces facing away from the stool holding bag 6 and oriented for attachment to the hook portion 22 secured on the bandage unit 9 positioned on the patient 16. A diaper 1 wrapped around the patient 16 and the stool holding bag 6, supports the weight of the stool holding bag 6 as it fills, and maintains the stool holding bag 6 in a position on a patient 16 where an incontinence pad (not shown) is typically worn. Super absorbent polymer (SAP) resin may also employed as an absorbent core in the present invention stool containment system structure. Super Absorbent Polymer (SAP) resin may also used as a part of the contoured pad 13, within the non-tapered bottom portion 25 of the stool holding bag 6, within diaper 1, or other present invention structure. Instead of SAP, or in addition to it, other non-toxic, non-irritating, non-corrosive, and super absorbent materials capable of absorbing approximately forty-to-sixty times their weight in fluid may be used. However, cellulose and other fiber-based products that only absorb approximately twenty times their weight in fluid may also be used, but are not preferred. It should also be noted that although four preferred embodiments are specifically disclosed herein, the present invention should not be considered as limited thereto, and one should consult the appended claims for a determination of the structure and scope of the present invention. FIGS. 1-2 disclose a first preferred embodiment of the present invention of a diaper 1 usable as a part of the present invention, while FIGS. 2a and 2b show a first preferred embodiment of the present invention respectively without and with diaper 1. Similarly, FIGS. 3a and 3b show a second preferred embodiment of the present invention respectively without and with diaper 1, and FIGS. 4 and 5 show the working relationship and positioning of backing member 19 and contoured pad 13 with respect to one another. FIGS. 6a and 6b show the generally C-shaped configuration of bandage unit 9 and its opposing surfaces, while FIGS. 7-8 show preferred positioning of bandage unit 9 and the combined backing unit 9 and contoured pad 13 on a patient 16. FIG. 9 discloses a third preferred embodiment of the present invention having an anti-reflux valve, while FIGS. 10-11 disclose a fourth preferred embodiment of the present invention intended for use with non-infectious stool that employs hook fasteners 22 to secure the non-tapered bottom portion 25 of a stool holding bag 6 to the underside surface of the top filament 11 of diaper 1. FIG. 12 shows a cutting tool 18 with a cutting head 29 and a handle 30 that can be configured and used to cut an opening 5 in the top filament 11 of diaper 1 or puncture perforations in the form of a cutting line 2 (as shown in FIG. 1a).

Figure 2B:
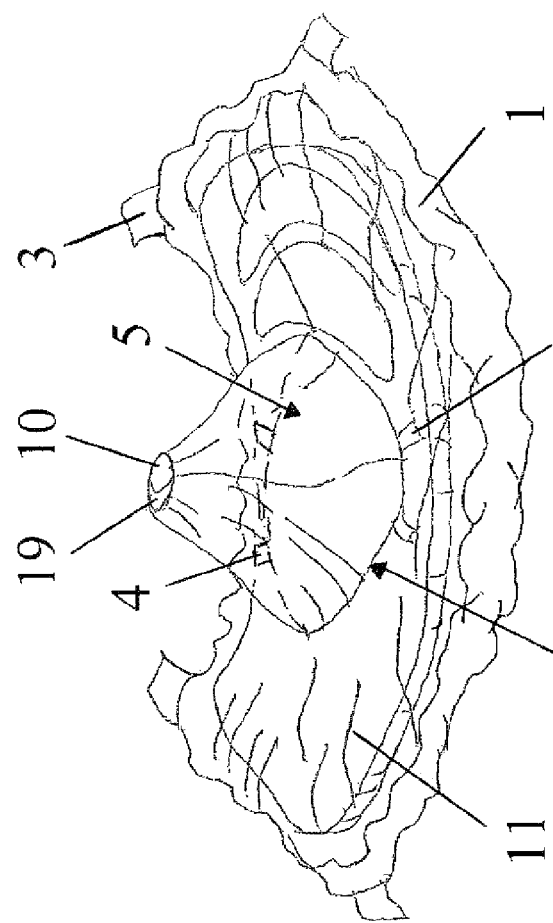
FIG. 2b is a perspective view from the top of a stool holding bag in a first preferred embodiment of the present invention supported by the diaper shown in FIG. 1, and showing the stool holding bag having urine transfer holes/areas in its non-tapered bottom portion that becomes inserted through the opening in the diaper created when the centrally located cut line is slit, with FIG. 2b also showing the tapered top portion of the stool holding bag extending upwardly beyond the top filament layer of the diaper, and a backing member and opening associated with the top end of the tapered portion of the stool holding bag which are used to assist the transfer of stool from a patient to the stool holding bag without leakage or channeling of patient skin.
Figure 2A:
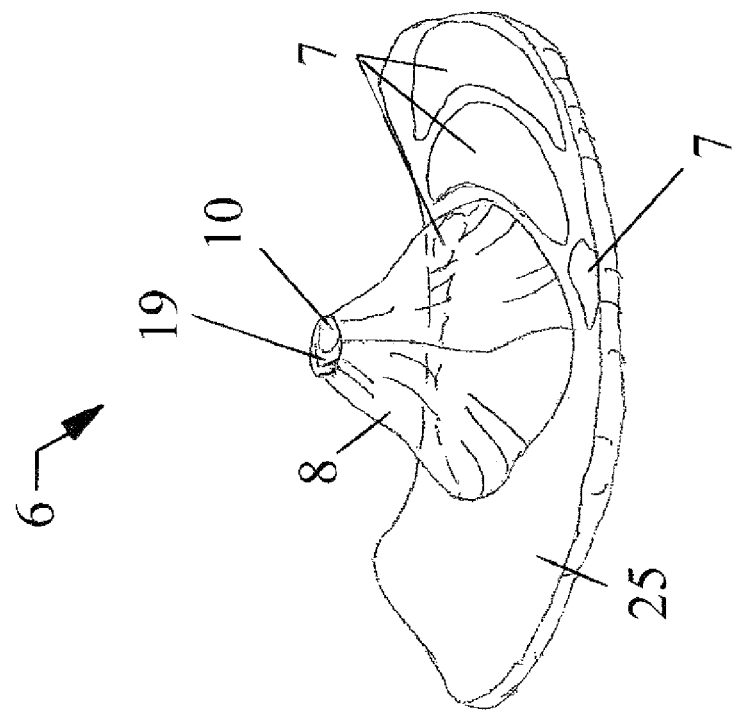
FIG. 2a is a perspective view from the top of a stool holding bag in a first preferred embodiment of the present invention and showing its non-tapered bottom portion with urine transfer holes/areas, and also showing the tapered top portion of the stool holding bag extending in an upwardly direction, and a backing member and opening associated with the top end of the tapered portion of the stool holding bag which are used to assist the transfer of stool from a patient to the stool holding bag without leakage or channeling of patient skin.

FIGS. 1-2 disclose a first preferred embodiment of the present invention of a diaper 1 usable as a part of the present invention. FIG. 1a is a perspective view from the top of a diaper 1 usable with a first preferred embodiment of the anti-channeling stool management system of the present invention to support its stool holding bag 6 in a desired position of use as it fills, and showing an optional cut line 2 for insertion of the non-tapered bottom portion 25 of the stool holding bag 6 of the present invention that allows repeat use of the diaper 1 at least once in many stool incontinence management applications. FIG. 1b is a perspective view from the top of the diaper in FIG. 1, and showing the cut line 2 open and attachable adhesive strips 4 used to create and maintain an opening 5 during insertion of the non-tapered bottom portion 25 of the stool holding bag 6 of the present invention. The top filament 11 of diaper 1 is also marked in FIGS. 1a and 1b, as it is the layer typically cut for assisting in stool holding bag 6 support and for infectious stool applications. The number 12 in FIG. 1b is used to identify the absorbent interior of diaper 1, which could include fiberfill or other absorbent material, and also preferably SAP.

FIGS. 2a and 2b show a first preferred embodiment of the present invention respectively without and with diaper 1. FIG. 2a is a perspective view from the top of a stool holding bag 6 in a first preferred embodiment of the present invention and showing its non-tapered bottom portion 25 with several urine transfer holes/areas 7, and also showing the tapered top portion 8 of the stool holding bag 6 extending in an upwardly direction, and a backing member 19 and opening 10 associated with the top end of the tapered portion 8 of the stool holding bag 6 which are used to assist the transfer of stool (not shown) from a patient 16 to the stool holding bag 8 without leakage or channeling of patient 16 skin. FIG. 2b is a perspective view from the top of a stool holding bag 6 in a first preferred embodiment of the present invention supported by the diaper 1 shown in FIG. 1, and showing the stool holding bag 8 having urine transfer holes/areas 7 in its non-tapered bottom portion 25 that becomes inserted through the opening 5 in the top filament 11 of diaper 1 created when the centrally located cut line 2 is slit (see FIG. 1a), with FIG. 2b also showing the tapered top portion 8 of the stool holding bag 6 extending upwardly beyond the top filament layer 11 of diaper 1, and a backing member 19 and opening associated with the top end 20 of the tapered portion 8 of the stool holding bag 6 which are used to assist the transfer of stool from a patient to the stool holding bag 6 without leakage or channeling of patient skin.

Similarly, FIGS. 3a and 3b show a second preferred embodiment of the present invention respectively without and with diaper 1. FIG. 3a is a perspective view from the top of a diaper insert (stool holding bag 6 with a liner 24) providing the second preferred embodiment of the present invention that is similar to the stool holding bag 6 shown in FIG. 2a, and showing the non-tapered bottom portion 25 of the stool holding bag 6 with urine transfer holes/areas 7, and also showing the tapered top portion 8 of the stool holding bag 6 extending in an upwardly direction, and a backing member 19 and opening 10 associated with the top end 20 of the tapered portion 8 of the stool holding bag 6 which are used to assist the transfer of stool from a patient 16 to the stool holding bag 6 without leakage or channeling of patient 16 skin. FIG. 3b is a perspective view from the top of the non-tapered bottom portion 25 of the diaper insert shown in FIG. 3a inside the diaper 1 shown in FIGS. 1a, 1b, and 2b. This embodiment is also contemplated for use with infectious stools.

FIGS. 4 and 5 show the working relationship and positioning of backing member 19 and contoured pad 13 with respect to one another, while FIGS. 6a and 6b show the generally C-shaped configuration of bandage unit 9 and its opposing surfaces, while FIGS. 7-8 show preferred positioning of bandage unit 9 and the combined backing unit 9 and contoured pad 13 on a patient 16. FIG. 4 is a top view of the generally C-shaped backing member 19 used as a part of preferred embodiments of the present invention, which is shown having the loop portion 21 of a 2-part fastener attached to it that can be releasably secured to the hook portion 22 of the 2-part fastener secured to the bandage unit 9 shown in FIGS. 6a and 6b, with the exterior perimeter curved edge of a present invention absorbent contour pad 13 shown partially overlapping the backing member 19 so that the surface of the contoured pad 13 can be secured by the backing member 19 which biases it against the bandage unit 9 in a position where the contoured pad 13 can absorb any small amount of stool that is adjacent to the opening 10 in the stool holding bag 6 and not readily transferred into it. Barrier cream or other skin protecting composition 23 is used adjacent to the contoured pad 13 as a further means of preventing stool from contacting patent 16 skin. FIG. 5 is a bottom view of the generally C-shaped backing member 19 shown in FIGS. 2a, 2b, 3a, and 3b, with FIG. 5 showing it attached to the top edge 20 of the present invention stool holding bag 6 and the backing member 19 overlapping part of an absorbent contoured pad 13 used as a part of the present invention adjacent to patient 16 skin near the rectal opening 28, with the loop portion 21 of a hook-and-loop fastener secured out-of-view on the reverse side of the backing member 19. FIG. 6a is a bottom view of the generally C-shaped bandage unit 9 having the hook 22 portion of a hook-and-loop fastener secured to it, and showing the hook fasteners 22 substantially covering the exterior surface of the bandage unit 9 that during use is positioned away from the patient's 16 skin and available for connection to the loop portion 21 of a hook-and-loop fastener secured to the backing member 19 attached to the top edge 20 of the present invention stool holding bag 6. FIG. 6b is a top view of the generally C-shaped bandage unit 9 having an adhesive surface 27 for attachment of bandage unit 9 to patient 16 skin, that allows its reverse side shown in FIG. 6a to become secured to the backing member 19 attached to the top edge 20 of the present invention stool holding bag 6. FIG. 7 is an enlarged view of the anal area of a patient with the generally C-shaped bandage unit 9 used as a part of the most preferred embodiments of the present invention in its position of use rearward from the rectal opening 28, with the hook portion 22 of a hook-and-loop fastener visible and the adhesive surface 27 out-of-view on the reverse side of the bandage unit 9. FIG. 8 is an enlarged view of the anal area of a patient 16 with the combined backing member 19 and contoured pad 13 shown in FIG. 5 and used as a part of the most preferred embodiments of the present invention in their positions of use rearward from the rectal opening 28.

Figure 10:
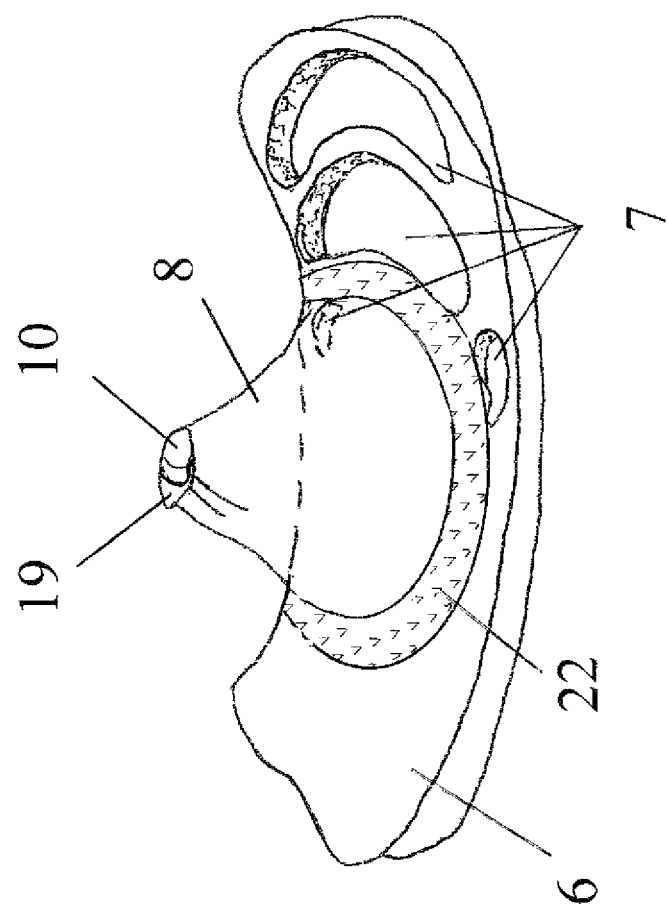
FIG. 10 is a perspective view from the top of a fourth preferred embodiment of the anti-channeling stool management system of the present invention, wherein hook fasteners secure the top of the stool holding bag to the inside top surface of the filament of a supporting diaper.
Figure 11:
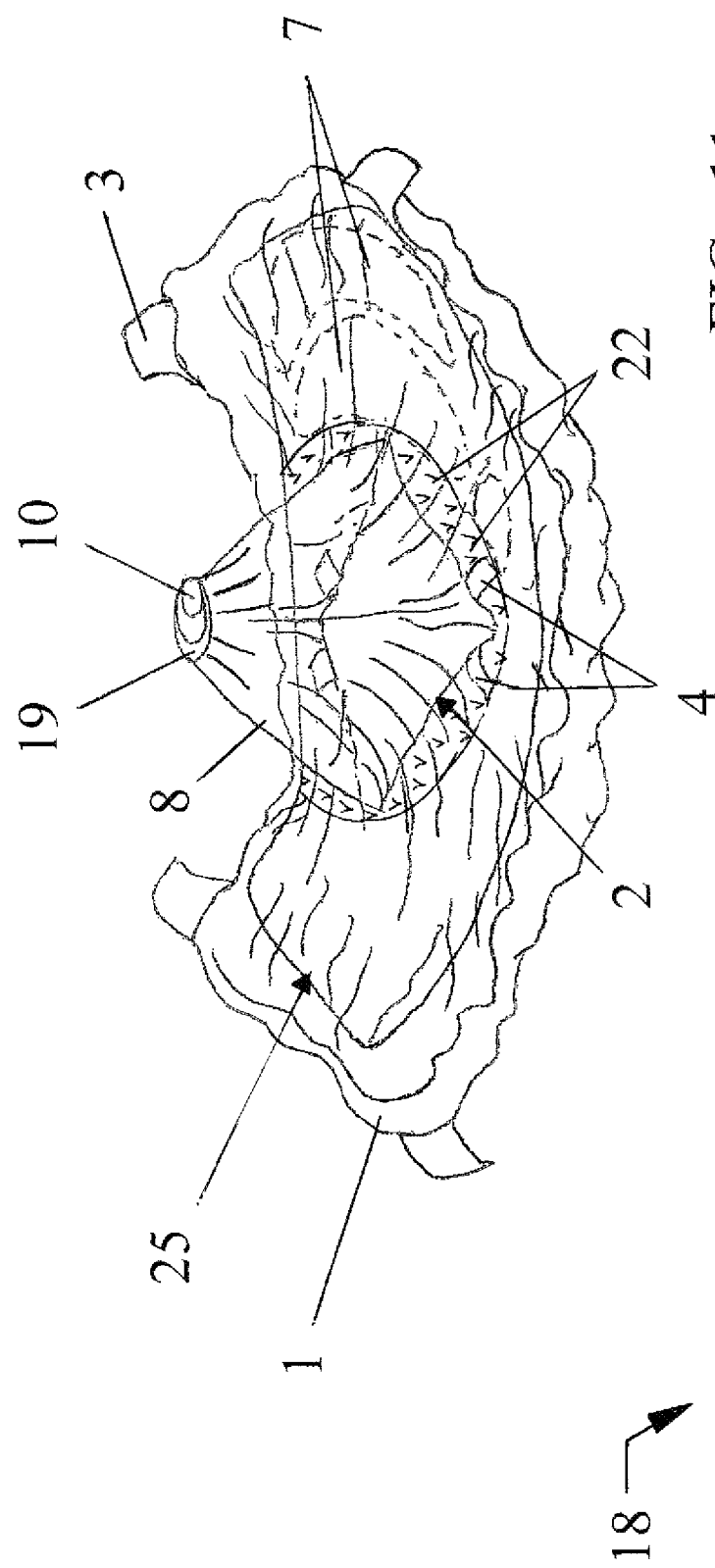
FIG. 11 is a perspective view from the top of a fourth preferred embodiment of the anti-channeling stool management system of the present invention, wherein hook fasteners secure the top of the non-tapered portion of the stool holding bag to the inside top surface of the filament of a supporting diaper.
Figure 12:
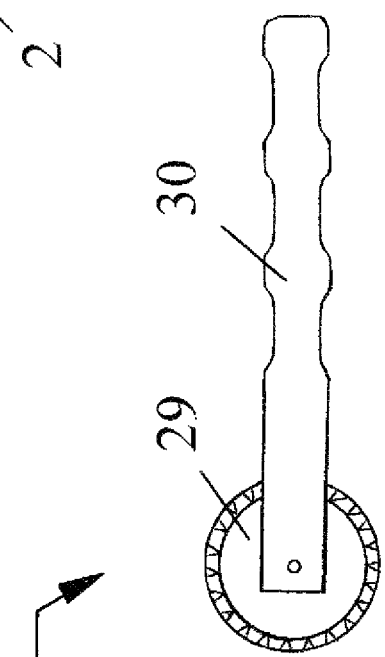
FIG. 12 is a perspective view of a cutting tool usable as a part of preferred embodiments of the present invention to slit the top filament of a diaper for insertion of a stool holding bag, at the cutting line, if present.

FIG. 9 discloses a third preferred embodiment of the present invention having an anti-reflux valve 17, while FIGS. 10-11 disclose a fourth preferred embodiment of the present invention intended for use with non-infectious stool that employs hook fasteners 22 to secure the non-tapered bottom portion 25 of a stool holding bag 6 to the underside surface of the top filament 11 of diaper 1. FIG. 9 is a perspective view from the top of the stool holding bag 6 in a third preferred embodiment of the present invention with a flap 17 of plastic positioned to block the top opening 10 in the stool holding bag 6 in a manner that prevents reflux movement of stool from the stool holding bag 6 and upward toward the patient 16. FIG. 10 is a perspective view from the top of a fourth preferred embodiment of the anti-channeling stool management system of the present invention, wherein hook fasteners 22 secure the top of the stool holding bag 6 to the inside top surface of the filament 11 of a supporting diaper 1. FIG. 11 is a perspective view from the top of a fourth preferred embodiment of the anti-channeling stool management system of the present invention, wherein hook fasteners 22 secure the top of the non-tapered bottom portion 25 of the stool holding bag 6 to the inside top surface of the filament 11 of a supporting diaper 1.

FIG. 12 shows a cutting tool 18 with a cutting head 29 and a handle 30 that can be configured and used to cut an opening 5 in the top filament 11 of diaper 1 or puncture perforations in the form of a cutting line 2 (as shown in FIG. 1a). The configuration of the cutting edge on the cutting head 29 and the handle 30 attached to the cutting head 29 are considered as representative, and not limiting. The dimensional proportions of the cutting head 29 and the handle 30 shown in FIG. 12 are also considered to be exemplary, and not critical.

While the written description of the invention herein is intended to enable one of ordinary skill to make and use its best mode, it should also be appreciated that the invention disclosure only provides examples of specific embodiments and methods, and many variations, combinations, and equivalents also exist which are not specifically mentioned. The present invention should therefore not be considered as limited to the above-described embodiments, methods, and examples, or the language in the accompanying Abstract, but instead encompassing all embodiments and methods within the scope and spirit of the invention as defined in the appended claims.

I claim:

1. A stool management and collection system for acutely and chronically ill patients, said system comprising:
a generally C-shaped absorbent contour pad;
a stool holding bag with a tapered upper portion extending in an upward direction and a top edge around an opening, said stool holding bag having an anti-reflux valve adjacent to said top edge, said anti-reflux valve configured to block the opening of said stool holding bag, said stool holding bag also having a non-tapered lower portion with at least one urine transfer hole located on said non-tapered lower portion;
a skin sealing composition;
a generally C-shaped backing member securing said top edge of said stool holding bag, said C-shaped backing member also having a first opposed surface and a second opposed surface, said first surface positioned adjacent to said stool holding bag, and said second surface positioned adjacent to said C-shaped absorbent contour pad, said second surface having an inner crescent portion adjacent to an outer crescent portion, with a first part and a second part of a two-part connectible and releasable fastener associated with said outer crescent portion, and said inner crescent portion is at least partially in contact with said contour pad; and a bandage unit having opposed sides and said second part of said two-part connectible and releasable fastener associated with one of said opposed sides, said bandage unit also having a skin-adhering substance associated with the other one of said opposed sides, wherein said bandage unit is capable of being fixed against a patient's skin around the rectal opening and sealed with said skin-sealing composition positioned between said bandage unit and the rectal opening, wherein, when said two parts of said easily connectible and releasable fastener are joined together, said stool collection system is attached to the skin around the patient's rectal opening with said skin-adhering substance, and said inner crescent portion biasing said contour pad toward said patient.

2. The system of claim 1, wherein said stool holding bag further comprises a substance capable of absorbing approximately forty to sixty times its weight in fluid.

3. The system of claim 2, wherein said substance is a super absorbent polymer.

4. The system of claim 2, wherein said substance is configured as a liner in said stool holding bag.

5. The system of claim 4, wherein said liner comprises a super absorbent polymer.

6. The system of claim 1, further comprising a diaper supporting said stool holding bag.

7. The system of claim 6, wherein said diaper has a cutting line and a plurality of pull tabs adjacent to said cutting line, facilitating the creation of an opening in said diaper for insertion of a portion of said stool holding bag.

8. A method for using the system of claim 7 and comprising the steps of:
   providing the system of claim 7 and a cutting tool;
   using said cutting tool against said cutting line to create an opening in said top filament of said diaper; and
   inserting a portion of said stool holding bag through said opening.

* * * * *